(12) United States Patent
Jung et al.

(10) Patent No.: US 11,331,441 B2
(45) Date of Patent: May 17, 2022

(54) INHALATION SYSTEM WITH COMPUTING DEVICE FOR TRANSMITTING SIGNALS

(71) Applicant: Presspart GmbH & Co. KG, Marsberg (DE)

(72) Inventors: Benjamin Jung, Cologne (DE); Arun Sarda, Lancashire (GB)

(73) Assignee: Presspart GmbH & Co. KG, Marsberg (DE)

( * ) Notice: Subject to any disclaimer, the term of this patent is extended or adjusted under 35 U.S.C. 154(b) by 314 days.

(21) Appl. No.: 16/176,103

(22) Filed: Oct. 31, 2018

(65) Prior Publication Data
US 2019/0151577 A1     May 23, 2019

(30) Foreign Application Priority Data
Nov. 20, 2017    (EP) ..................................... 17202620

(51) Int. Cl.
*A61M 15/00*     (2006.01)
*G16H 20/10*     (2018.01)
(Continued)

(52) U.S. Cl.
CPC ......... *A61M 15/008* (2014.02); *A61B 5/0022* (2013.01); *A61M 15/002* (2014.02);
(Continued)

(58) Field of Classification Search
CPC ............ A61M 15/008; A61M 15/0065; A61M 15/0068; A61M 15/007; A61M 15/0071;
(Continued)

(56) References Cited

U.S. PATENT DOCUMENTS 5,363,842 A * 11/1994 Mishelevich ............ A61N 7/00
                                                      128/200.14
5,392,768 A *  2/1995 Johansson ............. A61M 15/00
                                                      128/200.14
(Continued)

FOREIGN PATENT DOCUMENTS

DE      202017101591 U1   5/2017
EP          3363485 A1    8/2018
(Continued)

OTHER PUBLICATIONS

European communication dated Apr. 30, 2018 in corresponding European patent application No. 17202620.5.

*Primary Examiner* — Joseph D. Boecker
*Assistant Examiner* — Brian T Khong
(74) *Attorney, Agent, or Firm* — Nields, Lemack & Frame, LLC

(57) ABSTRACT

An inhalation system including a metered dose inhaler and a separate computing device. The inhaler includes a flow rate sensor for detecting an inhalation flow through the actuator housing upon patient inhalation and a transmitting unit for transmitting a signal of the at least first switch as well as of the flow rate sensor to the computing device. The computing device generates visual and/or acoustic messages independently of the signals of the at least one switch and the flow rate sensor in order to guide the patient through multiple steps. The computing device further evaluates the use of the inhaler by comparing the transmitted signals of the at least first switch and of the flow rate sensor with the visual and/or acoustic messages. The transmitting unit transmits the signals of the at least first switch and the flow rate sensor to the computing device after the use of the inhaler.

20 Claims, 1 Drawing Sheet

Figure 1:
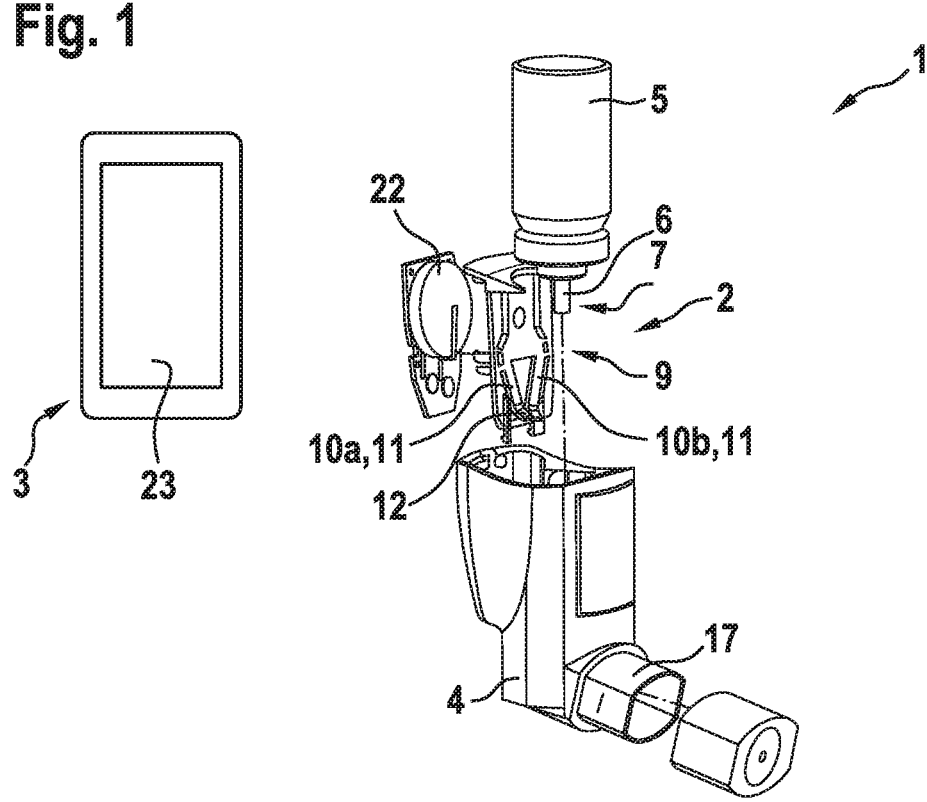

(51) Int. Cl.
  *A61B 5/00* (2006.01)
  *A61B 5/087* (2006.01)
  *A61M 16/00* (2006.01)
(52) U.S. Cl.
  CPC .......... *A61M 15/009* (2013.01); *G16H 20/10* (2018.01); *A61B 5/087* (2013.01); *A61B 5/4833* (2013.01); *A61B 5/742* (2013.01); *A61B 2560/0242* (2013.01); *A61M 15/0025* (2014.02); *A61M 2016/003* (2013.01); *A61M 2205/3327* (2013.01); *A61M 2205/3331* (2013.01); *A61M 2205/3334* (2013.01); *A61M 2205/3368* (2013.01); *A61M 2205/3561* (2013.01); *A61M 2205/3569* (2013.01); *A61M 2205/3576* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/581* (2013.01); *A61M 2205/583* (2013.01); *A61M 2205/702* (2013.01); *A61M 2205/8206* (2013.01); *A61M 2230/40* (2013.01); *A61M 2230/42* (2013.01)

(58) Field of Classification Search
  CPC .......... A61M 15/0073; A61M 15/0075; A61M 15/0076; A61M 15/0078; A61M 15/002; A61M 15/0021; A61M 15/009; A61M 15/0091; A61M 15/0025; A61M 2016/003; A61M 2016/0033; A61M 2016/0027; A61M 2016/0015; A61M 2016/0018; G16H 20/10; A61B 5/0022; A61B 5/002; A61B 5/0004; A61B 5/0024; A61B 5/087; A61B 5/4833; A61B 5/742; A61B 5/74; A61B 5/7405; A61B 5/7425; A61B 5/743; A61B 5/7435; A61B 5/746; A61B 5/7465; A61B 5/747; A61B 5/7475; A61B 5/748
  See application file for complete search history.

(56) References Cited

U.S. PATENT DOCUMENTS

| | | | | |
|---|---|---|---|---|
| 5,544,647 A * | 8/1996 | Jewett | .................. | A61M 15/009 128/200.23 |
| 5,809,997 A * | 9/1998 | Wolf | .................... | A61M 15/009 128/200.23 |
| 6,202,642 B1 * | 3/2001 | McKinnon | .......... | A61M 15/009 128/200.14 |
| 2004/0255936 A1 * | 12/2004 | Urbanus | ............. | A61M 15/008 128/200.23 |
| 2005/0028815 A1 * | 2/2005 | Deaton | ............... | A61M 15/008 128/200.23 |
| 2006/0237009 A1 * | 10/2006 | Jones | ................. | A61M 15/0093 128/203.15 |
| 2006/0254581 A1 * | 11/2006 | Genova | ............. | A61M 15/0065 128/200.23 |
| 2007/0084462 A1 * | 4/2007 | Allen | .................. | A61M 15/009 128/200.23 |
| 2007/0295329 A1 * | 12/2007 | Lieberman | .......... | A61M 15/008 128/200.23 |
| 2008/0173301 A1 * | 7/2008 | Deaton | ............. | A61M 15/0091 128/203.12 |
| 2009/0151721 A1 * | 6/2009 | Spaargaren | ......... | A61M 15/008 128/203.12 |
| 2009/0151723 A1 * | 6/2009 | Lang | ................... | A61M 15/008 128/203.15 |
| 2011/0225008 A1 * | 9/2011 | Elkouh | .................. | G16H 10/60 705/3 |
| 2011/0265788 A1 * | 11/2011 | Wu | ..................... | A61M 15/009 128/200.23 |
| 2014/0053833 A1 * | 2/2014 | Cline | .................. | A61M 15/008 128/203.12 |
| 2015/0273165 A1 * | 10/2015 | Hadash | .................. | G16H 20/00 128/203.14 |
| 2016/0038696 A1 * | 2/2016 | Duignan | ............. | A61M 15/009 128/200.23 |
| 2016/0051776 A1 * | 2/2016 | Von Hollen | ........ | A61M 15/008 128/200.23 |
| 2016/0082208 A1 * | 3/2016 | Ballam | ............... | A61M 16/024 128/200.14 |
| 2016/0144141 A1 * | 5/2016 | Biswas | ............... | A61M 15/009 128/200.23 |
| 2016/0144142 A1 * | 5/2016 | Baker | ............... | A61M 15/0021 128/200.23 |
| 2016/0255878 A1 * | 9/2016 | Huang | .................... | A61B 5/087 |
| 2016/0325057 A1 * | 11/2016 | Morrison | .......... | A61M 15/0026 |
| 2016/0325058 A1 * | 11/2016 | Samson | .................. | A61B 5/087 |
| 2016/0366939 A1 * | 12/2016 | Alarcon | ............... | A24F 47/008 |
| 2017/0157345 A1 * | 6/2017 | Panjabi | .................. | G06M 1/083 |
| 2017/0290527 A1 * | 10/2017 | Morrison | ............. | A61B 5/4833 |
| 2017/0325734 A1 * | 11/2017 | Sutherland | ........ | A61M 15/0051 |
| 2018/0093053 A1 | 4/2018 | Turner et al. | | |

FOREIGN PATENT DOCUMENTS

| | | | |
|---|---|---|---|
| WO | 2015/109259 A1 | 7/2015 | |
| WO | 2016/030521 A1 | 3/2016 | |
| WO | 2016/030844 A1 | 3/2016 | |
| WO | 2016/033421 A1 | 3/2016 | |
| WO | WO-2016030844 A1 * | 3/2016 | .......... A61M 15/009 |

* cited by examiner

INHALATION SYSTEM WITH COMPUTING DEVICE FOR TRANSMITTING SIGNALS

TECHNICAL FIELD

The present invention relates to an inhalation system comprising a metered dose inhaler for dispensing an aerosol dose during use and a separate computing device for computing signals received from the metered dose inhaler. The metered dose inhaler comprises an actuator housing in which an aerosol container with an activation valve is inserted. The container is configured to move in a longitudinal direction from a rest position to an activation position in which the valve is depressed against a bottom of the actuator housing such that an aerosol dose is released. A triggering unit comprises at least a first trigger member which is configured to interact with the container moving in the longitudinal direction. The at least first trigger member triggers at least a first switch of an electronic unit when the container reaches a first longitudinal position during its movement from the rest position to the activation position.

BACKGROUND OF THE INVENTION

Metered dose inhalers (MDIs) are medication delivery devices which deliver a pharmaceutical formulation including one or more pharmaceutical active compounds to a human or another mammalian patient. Typically, the pharmaceutical formulation is delivered by the MDIs in unit doses in the form of an aerosol. Each actuation of the MDIs delivers one unit dose. The unit dose is expelled by the MDIs and is taken into the body of the patient on inhalation, via the nose or mouth. The pharmaceutical formulation is delivered to or via the respiratory track, notably to the lungs, of the patient on inhalation. Metered dose inhalers are typically used for the treatment of respiratory infections and disorders including respiratory track infections, obstructive lung disease, inflammatory lung disease and chronic obstructive pulmonary disease. Asthma treatment is a particularly common use of MDIs.

Metered dose inhalers typically comprise a dose counter. Dose counters allow counting of the doses which are released from the container such that the patient inhaling the doses is always aware of the doses being left in the container. These dose counters may operate either mechanically or electromechanically.

There has been a recent development towards use of electronic dose counters, as they allow the implementation of additional functions such as monitoring functions or evaluation functions. Based on these additional functions a physician or the patient may for example monitor the frequency of dispensed doses and the point of time when these doses have been dispensed.

WO 2016/030844 A1 describes a metered dose inhaler with an actuator housing in which two separate trigger members are actuated by the container in two different positions of the container. The first trigger member is actuated upon displacement of the container from the rest position to a first position, thereby indicating that the user intends to dispense a dose of the aerosol. The container is then moved from the first position to a second position in which the valve is opened and the aerosol is dispensed. When the aerosol is dispensed, the second trigger member is actuated. Upon actuation the first and second trigger members trigger first and second switches of a circuit assembly. A counting circuit receives signals from the first and second switches when being triggered and counts the number of dispensed doses.

Co-pending European Patent Application No. 17156995.7 also discloses a metered dose inhaler with an actuator housing and an electronic dose counter. Upon movement of a container from a rest position to an activation position in which an aerosol dose is released, a single trigger member is actuated. Upon actuation the trigger member interacts with a switch generating an electrical signal that is transmitted to a processing unit. The metered dose inhaler further comprises a transmitting unit for wirelessly transmitting results processed by the processing unit. The results may be transmitted to a user's smartphone or any other electronic device.

Studies have shown that the effect of an inhaled pharmaceutical formulation is heavily dependent on, amongst others, the ability of the patient to inhale the right amount of the pharmaceutical formulation. It has been found that a lot of patients living with asthma do not use their inhaler adequately and thus do not receive the correct amount of medication upon inhalation. In particular, a lack of hand-breath coordination (press and breathe), an incorrect speed and/or depth of inhalation, an incorrect actuation of the canister and a missing breath-hold after inhalation of the dose of medicament are the most frequent errors when using an MDI. Thus, there is a need to implement guiding functions in the metered dose inhaler in order to help patients to adequately use their inhaler.

WO 2015/109259 A1 discloses a system comprising a pulmonary medication device and a separate computing device such as a smartphone. The pulmonary medication dosing device comprises a flow rate sensor to sense an inhalation flow of a patient. Moreover, the pulmonary medication device comprises an actuation sensor configured to detect actuation of a medication canister by which a dose of medicament is dispensed. Based on a signal of the flow rate sensor indicative of the sensed inhalation flow, the computing device generates an alert that instructs a user to actuate the medication canister. This requires a stable connection between the flow rate sensor and the smartphone in order to transmit data of the flow rate sensor to the smartphone and generate the alert within a predefined time interval after start of the inhalation. In case of connection problems between the flow rate sensor and the computing device, the alert may be generated too late or not at all. In either case the ideal point of time to actuate the canister may be missed.

It is an object of the present invention to provide a cost-effective and highly reliable inhalation system which simplifies the correct use of a metered dose inhaler.

SUMMARY OF THE INVENTION

This object is achieved by an inhalation system comprising the features of claim 1. Preferred embodiments are set out in the dependent claims.

According to the present invention, the metered dose inhaler comprises a flow rate sensor for detecting an inhalation flow through the actuator housing during use of the metered dose inhaler upon inhalation by a patient. The metered dose inhaler further comprises a transmitting unit for transmitting a signal of the at least first switch indicating a first time when the first switch is triggered by the first trigger member and a signal of the flow rate sensor to the computing device. The computing device is configured to generate visual and/or acoustic messages independently of the signals of the at least first switch and the flow rate sensor in order to guide the patient through multiple steps of the use of the metered dose inhaler. The computing device is further configured to evaluate the use of the metered dose inhaler by comparing transmitted signals of the at least first switch and of the flow rate sensor with the visual and/or acoustic messages and/or with predefined data which corresponds to an ideal use of the metered dose inhaler. Moreover, the transmitting unit is configured to transmit the signals of the at least first switch and the flow rate sensor to the computing device during and/or after the use of the metered dose inhaler.

The transmitting unit may be configured to directly transmit the signals of the at least first switch and the flow rate sensor to the computing device. However, the transmitting unit may also be configured to transmit the signals of the at least first switch and the flow rate sensor to a cloud-based server system, e.g. via NB-IoT (NarrowBand-Internet of things), which then transmits said signals to the computing device. Alternatively the computing device may also request transmittal of said signals from the cloud-based server system.

The general function of the triggering unit comprising two trigger members is disclosed in International Patent Application WO 2016/030844 A1 which is herewith incorporated by reference in its entirety. Moreover, the general function of the triggering unit comprising one single trigger member is disclosed in European Patent Application No. 17156995.7 which is herewith incorporated by reference in its entirety, also. The triggering unit together with the electronic unit has proven to provide reliable detection of actuation of the medicament container and, thus, reliable counting of the released aerosol doses. In particular, it is advantageous to install the triggering unit in the interior of the actuator housing, as this avoids unintended dose counts, for example when the metered dose inhaler is dropped on the floor.

In connection with the present invention the term "use of the metered dose inhaler" has to be understood as the process applied by a patient in order to deliver an aerosol dose dispensed by a metered dose inhaler to or via the respiratory track, notably to the lungs, of the patient. This process may include multiple steps such as the inhalation of an inhalation flow, the actuation of the canister and/or the holding of breath after inhalation. Optionally, the process does not include the step of holding breath after inhalation. Moreover, the process may also include one or more steps of preparing the metered dose inhaler for dispensing an aerosol dose, such as shaking of the inhaler and/or priming. However, the term "use of the metered dose inhaler" refers to a single use of the metered dose inhaler during which in general one single aerosol dose is dispensed and inhaled.

Based on the visual and/or acoustic messages generated by the computing device, the patient receives instructions how to use the metered dose inhaler in a correct way. Following the instructions increases the effectiveness of the use of the metered dose inhaler which means that the correct amount of pharmaceutical formulation as dispensed by the canister is inhaled and the dispensed aerosol dose is allowed to fully impact on the patient's body. As the instructions are given independently of any signals of the metered dose inhaler, the instructions are not subjected to any delays caused by connection problems between the metered dose inhaler and the computing device. The signals of the switch and the flow rate sensor may be transmitted to the computing device during and/or subsequent to the use of the metered dose inhaler or at a later point of time.

According to an embodiment of the present invention, the transmission unit is configured to check during and/or subsequent to the use of the metered dose inhaler whether a connection is established between the transmitting unit and the computing device and, given that a connection is established, to transmit the signals of the at least first switch and of the flow rate sensor to the computing device. Preferably, the transmission unit is configured to check whether a connection is established once during and/or subsequent to the use of the metered dose inhaler. In case a connection is established, the signals of the at least first switch of the flow rate sensors are transmitted subsequently. Further attempts to check a connection between the metered dose inhaler and the computing device may be omitted in order to save energy.

Optionally, the computing device or the metered dose inhaler is configured to establish a connection to the respective other one upon an input by the user. The user may manually establish a connection between the metered dose inhaler and the computing device and thus a transmittance of the signals several hours or days after using the metered dose inhaler. In order to provide this time-shifted transmittance of the signals to the computing device, the electronic unit may comprise a storage device in order to save the signals of the at least one switch as well as of the flow rate sensor.

In a further embodiment of the present invention, the computing device is configured to generate visual and/or acoustic messages independently of the signals of the at least one switch and the flow rate sensor in order to guide the patient through the steps of starting inhalation, moving the canister from the rest position into the activation position and holding breath for a predefined period of time subsequent to inhalation. By receiving the messages from the computing device, the patient learns the timely sequence of the single steps of use of the metered dose inhaler. In addition, the patient gets used to the time intervals inbetween the single steps of use and thus to their timing.

According to another embodiment of the present invention, the computing device is configured to generate visual and/or acoustic messages independently of the signals of the at least one switch and the flow rate sensor in order to guide the patient through the steps of shaking and/or priming of the metered dose inhaler prior to inhalation. Shaking and/or priming of the metered dose inhaler prior to inhalation ensures that the components contained in the canister are properly mixed and uniformly spread in the canister. Thus, the steps of shaking and/or priming of the metered dose inhaler ensure that the dispensed aerosol dose upon actuation of the canister contains the intended dose of medicament.

Preferably, the computing device is configured to evaluate the use of the metered dose inhaler by comparing the timing of the transmitted signals of the at least first switch and of the flow rate sensor with the timing of the visual and/or acoustic messages. Optionally, the computing device is configured to evaluate the use of the metered dose inhaler by comparing the time differences between the transmitted signals with the time differences of the visual and/or acoustic messages. In order to determine the effectiveness of the use of the metered dose inhaler, the time difference between the start of inhalation and the actuation of the canister as well as optionally the duration of breath hold subsequent to inhalation is of particular relevance. In case the time difference between inhalation and actuation of the canister as well as optionally the period of breath hold correlate to predefined time intervals, the use of the metered dose inhaler may be identified as an effective use. Preferably, the computing device (3) is configured to evaluate the use of the metered dose inhaler (2) by analyzing the amount of the inhalation flow and preferably its run measured by the flow rate sensor. The computing device may for example be configure to compare the amount and/or the run of the inhalation flow to predefined data which corresponds to an ideal use of the metered dose inhaler. Those data may relate to the total amount but also to the constancy of the inhalation flow. Optionally, the computing device is configured to evaluate the use of the metered dose inhaler by comparing the timing of the transmitted signals of the at least first switch and of the flow rate sensor with predefined data which corresponds to an ideal use of the metered dose inhaler. Preferably, the computing device is further configured to generate additional visual and/or acoustic messages relating to the effectiveness of the use of the metered dose inhaler subsequent to evaluation of the corresponding use. The computing device may be configured to generate visual and/or acoustic messages stating whether the use of the metered dose inhaler was effective or ineffective or to generate a number stating how effective the use of the metered dose inhaler was.

Also preferred is an embodiment of the present invention according to which the computing device comprises a display, wherein the visual and/or acoustic messages are contained in a video clip which is shown on the display of the computing device. Optionally, the video clip contains several written messages when to start the multiple steps of the use of the metered dose inhaler. Alternatively, the video clip may show the application of the metered dose inhaler in pictures.

According to a further embodiment, the first trigger member is designed as flexible tongue having an end portion configured to interact with the container moving from the rest position to the activation position. Preferably, the container laterally bends the trigger member upon movement of the container in a longitudinal direction from the rest position to the activation position.

According to another embodiment, the triggering unit comprises a second trigger member and the electronic unit has a substrate with a second switch thereon, the second switch being configured to interact with the second trigger member when the container moves from the rest position to the activation position such that the second trigger member triggers the second switch when the container reaches a second longitudinal position that is different from the first longitudinal position during movement of the container from the rest position to the activation position. Using two trigger members instead of one single trigger member allows a more precise detection of the movement of the container from the rest position to the activation position. In particular, the use of two trigger members allows detection of a speed of the container moving from the rest position to the activation position. In case the time interval inbetween the triggering of the first and second trigger members is below and/or above a predefined threshold indicating that the canister is travelling at a sufficient speed, actuation of the canister and thus release of an aerosol dose is to be expected. Preferably, the transmitting unit is configured to also transmit a signal of the second switch indicating a second time when the second switch is triggered by the second trigger member to the computing device.

Preferably, the first and second trigger members are designed as flexible tongues, each having an end portion configured to interact with the container moving from the rest position to the activation position. Preferably, the first and second trigger members extend from a backside of the actuator housing diagonally to a mouthpiece located on a front side of the actuator housing opposite the back side. The trigger members are configured to be bent laterally to the longitudinal direction of the container being moved from the rest position to the actuation position upon movement of the container. Accordingly, the electronic unit comprising the first and second switches is positioned at the backside of the actuator housing. However, it is also possible to position the electronic unit at the front side of the actuator housing. Accordingly, the trigger members extend diagonally from the front side to the backside of the actuator housing.

According to another embodiment of the invention, the flow rate sensor is configured to be brought from a sleep mode into an active mode by triggering the first switch when the container reaches the first longitudinal position during movement of the container from the rest position to the activation position or by the computing device when generating a visual and/or acoustic message, wherein in the sleep mode the flow rate sensor is deactivated and wherein in the active mode the flow rate sensor is capable of sensing an inhalation flow. Preferably, the electronic unit as well as the flow rate sensor connected thereto are powered by a power source such as a battery. Thus, there is a need to reduce the energy consumption of the inhalation system in order to increase the life-time of the battery. By configuring the flow rate sensor such that the sensor may be brought into a sleep mode during non-use of the inhalation system, the power consumption of the inhalation system is decreased.

Also preferred is an embodiment according to which the flow rate sensor is configured to be brought from a sleep mode into an active mode by the computing device when generating a visual and/or acoustic message, wherein in the sleep mode the flow rate sensor is deactivated and wherein in the active mode the flow rate sensor is capable of sensing an inhalation flow. Bringing the flow rate sensor into an active mode upon generating a visual and/or acoustic message allows the activation of the flow rate sensor independently of one or more trigger members. Preferably, the flow rate senor is brought into an active mode at the same time or prior to the point of time when the computing device instructs the patient to start inhalation.

In an embodiment of the present invention the metered dose inhaler and/or the computing device comprise one or several sensors for measuring temperature and/or humidity and/or one or several sensors for taking a reading of amount and size of dust particles in ambient air, and/or hazardous gases like smoke, carbon dioxide, cigarette smoke, smog, nitrogen compounds, ammonia or alcohol. Additional sensors which, for example, sense ambient air of the metered dose inhaler allow better understanding of when a patient uses the metered dose inhaler. Thus, additional sensors help physicians to diagnose and manage asthma to prevent severe attacks. Moreover, the metered dose inhaler and/or the computing device may comprise a Global Positioning System sensor (GPS sensor) for sensing and tracking the position of the inhaler. Preferably, the computing device is configured to combine data of different sensors and/or data of different sensors with data stored for example on a cloud based server system and/or data of different sensors with data which is entered by the patient and/or data of different sensors with data captured by other devices used by the patient. Combining such data may for example be useful when evaluating the use of the metered dose inhaler or to evaluate compliance of the patient with a medication plan.

Preferably, the flow rate sensor is a differential pressure sensor. In order to sense a flow rate along a flow path, sensation of a pressure difference along the flow path is of advantage. The differential pressure sensor is capable of measuring such a pressure difference, wherein each pressure is connected to opposite sides of the sensor. Thus, compared to the use of two separate pressure sensors, the differential pressure sensor needs a smaller installation space and reduces the cabling effort for connecting the sensor to the electronic unit.

Preferably, the flow rate sensor is positioned in the actuator housing, preferably in proximity to a mouthpiece of the metered dose inhaler. Optionally, the flow rate sensor is fixed to an inner side of the housing in proximity to a mouthpiece. As the inhalation flow containing inhaled air as well as the dispensed aerosol dose entrained in the inhaled air exits the metered dose inhaler through the mouthpiece, positioning of the flow rate sensor in proximity thereto allows measurement of the inhalation flow in total and not only the measurement of components (air flow or aerosol dose) thereof. Alternatively, the flow rate sensor may be positioned on the substrate of the electronic unit. This is a cost effective way to position the flow rate sensor as wiring between the electronic unit and the flow rate sensor is omitted.

Figure 2:
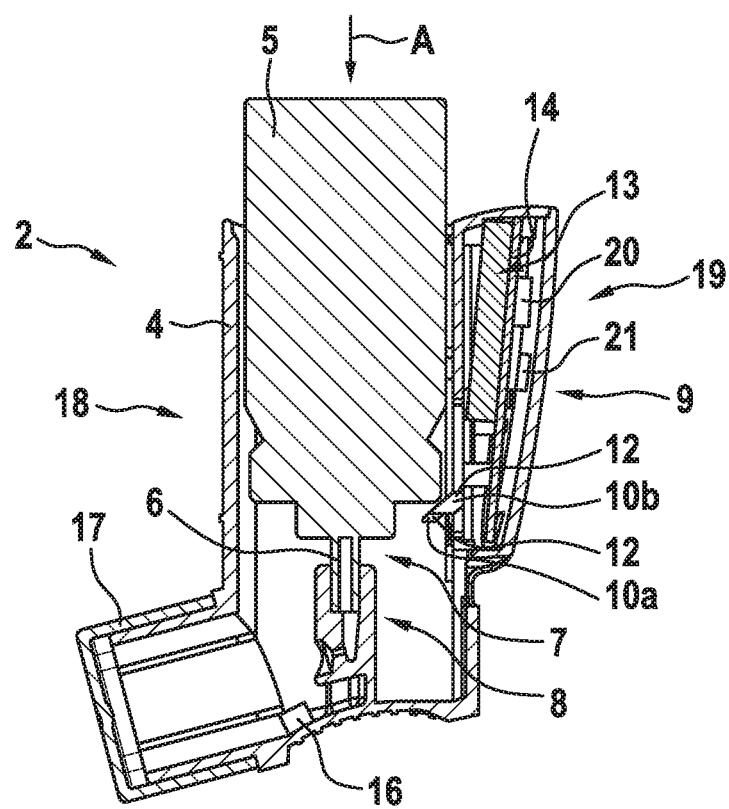

The invention will now be described in connection with one exemplary embodiment shown in the figures in which:

FIG. 1 shows a perspective view of an inhalation system according to the present invention and FIG. 2 shows a cross-sectional view of the metered dose inhaler of FIG. 1.

FIGS. 1 and 2 show an inhalation system 1 comprising a metered dose inhaler 2 for dispensing an aerosol dose during use and a computing device formed as a smartphone 3. The smartphone 3 is adapted to compute signals received from the metered dose inhaler 2 and is formed separately from the metered dose inhaler 2.

The metered dose inhaler 2 comprises an actuator housing 4 adapted to receive an aerosol container 5 with an activation valve 6 at a valve end 7 of the container 5. The container 5 is configured to move in a longitudinal direction A from a rest position to an activation position in which the valve 6 is depressed against a bottom portion 8 of the actuator housing 4 such that an aerosol dose is released.

The metered dose inhaler 2 further comprises a triggering unit 9 comprising first and second trigger members 10a, 10b, each being configured to interact with the container 5 when the container 5 moves in the longitudinal direction A from the rest position to the activation position. The first and second trigger members 10a, 10b are designed as flexible tongues 11, each having an end portion 12 configured to interact with the container 5 moving from the rest position to the activation position.

The metered dose inhaler 2 further comprises an electronic unit 13 having a substrate 14 with first and second switches 15a, 15b thereon. The first switch 15a is configured to interact with the first trigger member 10a when the container 5 moves from the rest position to the activation position such that the first trigger 10a triggers the first switch 15a when the container 5 reaches a first longitudinal position during movement of the container 5 from the rest position to the activation position. The second switch 10b is also configured to interact with the second trigger member 15b when the container 5 moves from the rest position to the activation position such that the second trigger member 10b triggers the second switch 15b when the container 5 reaches a second longitudinal position that is different from the first longitudinal position during movement of the container 5 from the rest position to the activation position. The detailed function of a metered dose inhaler as described above, is disclosed in WO 2016/030844 A1 which is herewith incorporated by reference in its entirety.

The metered dose inhaler 2 further comprises a flow rate sensor which is a differential pressure sensor 16 for detecting an inhalation flow through the actuator housing 4. The differential pressure sensor 16 is positioned in the actuator housing 4 in proximity to a mouthpiece 17 of the metered dose inhaler 2. The mouthpiece 17 is located at a front side 18 of the actuator housing 4 opposite a back side 19 of the actuator housing 4.

The differential pressure sensor 16 is configured to be brought from a sleep mode into an active mode by triggering the first switch 15a when the container 5 reaches the first longitudinal position during movement of the container 5 from the rest position to the activation position. In sleep mode the differential pressure sensor 16 is deactivated, whereas in the active mode the differential pressure sensor 16 is capable of sensing an inhalation flow.

Moreover, the metered dose inhaler 2 comprises a transmitting unit 20 for transmitting a signal of the first and second switches 10a, 10b as well as of the differential pressure sensor 16 to the smartphone 3. The signals of the first and second switches 15a, 15b indicate a first and second time when the first and second switches 15a, 15b are triggered by the first and second trigger members 10a, 10b, respectively. The signal of the differential pressure sensor 16 indicates a presence and/or a flow rate of the inhalation flow through the actuator housing 4 of the metered dose inhaler 2.

The transmitting unit 20 is part of the electronic unit 13 which additionally comprises a storage unit 21 for storing the signals received from the first and second switches 15a, 15b as well as from the differential pressure sensor 16. The storage unit 21 may be designed as a hard disk, a flash memory or any other memory for electronic data known in the prior art.

The storage unit may optionally be part of the transmitting unit such as e.g. a Bluetooth transmitting unit.

Additionally, the electronic unit 13 comprises a power source formed as a battery 22 for providing the electronic unit and any other electronic components of the metered dose inhaler 2 with power.

The transmitting unit 20 is configured to transmit the signals of the first and second switches 15a, 15b and the differential pressure sensor 16 to the smartphone 3 after the use of the metered dose inhaler 2. In other words: The transmitting unit is configured to transmit the signals of the first and second switches 15a, 15b and the differential pressure sensor 16 after a patient has stopped inhaling the aerosol dose dispensed by the metered dose inhaler 2 and after the patient held its breath for a predetermined duration of time.

The transmitting unit 20 is further configured to check during and/or subsequent to the use of the metered dose inhaler whether a connection is established between the transmitting unit 20 and the smartphone 3. Given that a connection is established, the transmitting unit 20 is configured to transmit the signals of the first and second switches 15a, 15b and of the differential pressure sensor to the smartphone 3. However, the smartphone 3 may also be configured to establish a connection between the metered dose inhaler 2 and the smartphone 3 upon a manual actuation by a user and thus to request transmittance of signals by the transmitting unit 20 several minutes, hours or days after using the metered dose inhaler 2.

The smartphone 3 is configured to generate visual and/or acoustic messages independently of the signals of the first and second switches 15a, 15b and the differential pressure sensor 16 in order to guide the patient through multiple steps of the use of the metered dose inhaler 2. These multiple steps may include the steps of shaking and/or priming of the metered dose inhaler 2 prior to inhalation and/or the steps of starting inhalation by the patient, moving the container 5 from the rest position into the activation position and holding breath for a predefined period of time subsequent to inhalation.

The smartphone 3 comprises a display 23, wherein the visual and/or acoustic messages are contained in a video clip which is shown on the display 23.

The smartphone 3 is further configured to evaluate the use of the metered dose inhaler 2 by comparing the transmitted signal of the first and second switches 15a, 15b and of the differential pressure sensor 16 with the visual and/or acoustic messages. In other words: The computing device is configured to evaluate the use of the metered dose inhaler 2 after the metered dose inhaler 2 has been used by the patient for dispensing and inhaling an aerosol dose.

The smartphone 3 is further configured to evaluate the use of the metered dose inhaler 2 by comparing the timing, in particular the time difference of the transmitted signals of the first and second switches 15a, 15b and of the differential pressure sensor 16 with the timing, in particular the time differences of the visual and/or acoustic messages. For example, a first time difference between the signal of the differential pressure sensor 16 indicating the presence of an inhalation flow through the actuator housing 4 and the signal of the second switch 15b indicating, for example, that the container was moved to the activation position such that an aerosol dose is released, is compared to a second time difference between the corresponding visual and/or acoustic messages instructing the patient to start inhalation and to move the container from the rest position into the activation position. If the first time difference is identical or lies in a band of tolerance compared to the second time difference the use of the metered dose inhaler 2 is determined an "effective" use. The smartphone 3 may be configured to display a corresponding message determining the use of the metered dose inhaler 2 as an "effective" use on the display 23.

Accordingly, when the evaluated time difference between the signal of the differential pressure sensor 16 and the signal of the second switch 15b is much bigger than the difference between the corresponding visual and/or acoustic messages such that a predefined threshold is exceeded, the smartphone 3 determines the use of the metered dose inhaler 2 as an "ineffective" use and may display a corresponding message on the display 23.

The smartphone 3 is also configured to bring the differential pressure sensor 16 from a sleep mode into an active mode when generating a visual and/or acoustic message. For example, the visual and/or acoustic messages may be started by a patient intending to use the metered dose inhaler 2, wherein the computing device is configured to send a corresponding signal to the differential pressure sensor 16 upon start of the visual and/or acoustic messages in order to bring the differential pressure sensor 16 into an active mode.

Moreover, the metered dose inhaler 2 and/or the smartphone 3 may comprise a sensor for measuring temperature and humidity and/or a sensor for taking a reading of amount and size of dust particles in ambient air as well as hazardous gases like smoke, carbon dioxide, cigarette smoke, smog, nitrogen compounds, ammonia or alcohol. Alternatively, the metered dose inhaler 2 and/or the smartphone 3 may be connected to a further device such as a watch which comprises such sensors. The watch (not shown) is configured to transmit the corresponding sensor data to the metered dose inhaler 2 and/or the smartphone 3.

REFERENCE NUMERALS 1 inhalation system
2 metered dose inhaler
3 smartphone (computing device)
4 actuator housing
5 aerosol container
6 activation device
7 valve end
A longitudinal direction
8 bottom portion
9 triggering unit
10a/b first/second trigger members
11 flexible tongues
12 end portion
13 electronic unit
14 substrate
15a/b first/second switches
16 differential pressure sensor (flow rate sensor)
17 mouthpiece
18 front side
19 back side
20 transmitting unit
21 storage unit
22 battery
23 display

The invention claimed is:
1. Inhalation system comprising:
a metered dose inhaler for dispensing an aerosol dose during use and
a separate computing device for computing signals received from the metered dose inhaler,
the metered dose inhaler comprising:
an actuator housing adapted to receive an aerosol container with an activation valve at a valve end of the container, the container being configured to move in a longitudinal direction from a rest position to an activation position in which the valve is depressed against a bottom portion of the actuator housing such that an aerosol dose is released,
a triggering unit comprising at least a first trigger member configured to interact with the container when the container moves in the longitudinal direction from the rest position to the activation position and
an electronic unit having a substrate with at least a first switch thereon, the first switch being configured to interact with the first trigger member when the container moves from the rest position to the activation position such that the first trigger member triggers the first switch when the container reaches a first longitudinal position during movement of the container from the rest position to the activation position,
wherein
the metered dose inhaler further comprises:
a flow rate sensor for detecting an inhalation flow through the actuator housing during use of the metered dose inhaler upon inhalation by a patient and
a transmitting unit for transmitting a signal of the at least first switch as well as of the flow rate sensor to the computing device,
wherein the signal of the first switch indicates a first time when the first switch is triggered by the first trigger member and, wherein the signal of the flow rate sensor indicates a presence and/or a flow rate of the inhalation flow and, wherein the computing device for computing signals received from the metered dose inhaler is formed as a smart phone and is configured to generate visual and/or acoustic messages independently of the signals of the at least first switch and the flow rate sensor in order to guide the patient through multiple steps of the use of the metered dose inhaler, whereby said visual and/or acoustic messages are not subjected to any delays caused by connection problems between the transmitting unit and the computing device and to evaluate the use of the metered dose inhaler by comparing the transmitted signals of the at least first switch and of the flow rate sensor with the visual and/or acoustic messages and/or with predefined data, wherein the transmitting unit is configured to check during and/or subsequent to use of the metered dose inhaler whether a stable connection is established between the transmitting unit and the computing device, and is configured to transmit the signals of the at least first switch and the flow rate sensor to the computing device after the use of the metered dose inhaler once such a stable connection is established;

and wherein the actuator housing further comprises a mouth piece for inhalation of the aerosol, wherein the triggering unit is positioned within the actuator housing opposite to the mouth piece, wherein the actuator housing is adapted to receive the aerosol container in between the triggering unit and the mouth piece.

2. Inhalation system according to claim 1 wherein the transmitting unit is configured to check during and/or subsequently to the use of the metered dose inhaler whether the connection is established between the transmitting unit and the computing device and, given that a connection is established, to transmit the signals of the at least first switch and of the flow rate sensor to the computing device.

3. Inhalation system according to claim 1, wherein the computing device is configured to generate the visual and/or acoustic messages independently of the signals of the at least one switch and the flow rate sensor in order to guide the patient through the steps of starting inhalation, moving the container from the rest position into the activation position and holding breath for a predefined period of time subsequent to inhalation.

4. Inhalation system according to claim 1, wherein the computing device is configured to generate the visual and/or acoustic messages independently of the signals of the at least first switch and the flow rate sensor in order to guide the patient through the steps of shaking and/or priming of the metered dose inhaler prior to inhalation.

5. Inhalation system according to claim 1, wherein the computing device is configured to evaluate the use of the metered dose inhaler by comparing the timing of the transmitted signals of the at least first switch and of the flow rate sensor with the timing of the visual and/or acoustic messages and/or with predefined data.

6. Inhalation system according to claim 1, wherein the computing device is configured to evaluate the use of the metered dose inhaler by analyzing an amount of the inhalation flow and/or the run of the inhalation flow measured by the flow rate sensor.

7. Inhalation system according to claim 1, wherein the computing device comprises a display, wherein the visual and/or acoustic messages are contained in a video clip which is shown on the display of the computing device.

8. Inhalation system according to claim 1, wherein the first trigger member is designed as a flexible tongue having an end portion configured to interact with the container moving from the rest position to the activation position.

9. Inhalation system according to claim 8 wherein the flow rate sensor is configured to be brought from a sleep mode into an active mode by triggering the first switch when the container reaches the first longitudinal position during movement of the container from the rest position to the activation position or by the computing device when generating a visual and/or acoustic message, wherein in the sleep mode, the flow rate sensor is deactivated and, wherein in the active mode, the flow rate sensor is capable of sensing the inhalation flow.

10. Inhalation system according to claim 1, wherein the triggering unit comprises a second trigger member and, that the electronic unit has the substrate with a second switch thereon, the second switch being configured to interact with the second trigger member when the container moves from the rest position to the activation position such that the second trigger member triggers the second switch when the container reaches a second longitudinal position that is different from the first longitudinal position during movement of the container from the rest position to the activation position.

11. Inhalation system according to claim 10, wherein the first and the second trigger member are designed as flexible tongues each having an end portion configured to interact with the container moving from the rest position to the activation position.

12. Inhalation system according to claim 1, wherein the flow rate sensor is configured to be brought from a sleep mode into an active mode by the computing device when generating a visual and/or acoustic message wherein in the sleep mode the flow rate sensor is deactivated and, wherein in the active mode the flow rate sensor is capable of sensing an inhalation flow.

13. Inhalation system according to claim 1, wherein the computing device comprises a sensor for measuring temperature, a sensor for measuring humidity and/or a sensor for taking a reading of amount and size of dust particles in ambient air-or hazardous gases.

14. Inhalation system according to claim 1, wherein the flow rate sensor is a differential pressure sensor.

15. Inhalation system according to claim 1, wherein the flow rate sensor is positioned in the actuator housing.

16. The inhalation system according to claim 15, wherein the flow rate sensor is positioned in the actuator housing in proximity to a mouthpiece of the metered dose inhaler.

17. The inhalation system according to claim 15, wherein the flow rate sensor is positioned in the actuator housing on the substrate of the electronic unit.

18. Inhalation system according to claim 1, wherein the computing device is configured to combine data of different sensors or data of different sensors with data stored or data of different sensors with data which is entered by a patient or data of different sensors with data captured by other devices used by the patient in order to evaluate the use of the metered dose inhaler or to evaluate compliance of the patient with a medication plan.

19. The inhalation system of claim 18, wherein the data is stored on a cloud based server system.

20. Inhalation system according to claim 1, wherein the metered dose inhaler comprises a sensor for measuring temperature, a sensor for measuring humidity and/or a sensor for taking a reading of amount and size of dust particles in ambient air or hazardous gases.

\* \* \* \* \*